United States Patent [19]
Kjell et al.

[11] Patent Number: 4,636,483
[45] Date of Patent: Jan. 13, 1987

[54] PHOSPHORUS CONTAINING ALUMINA CATALYST FOR THE PRODUCTION OF AROMATICS

[75] Inventors: Solveg S. Kjell, Euless, Tex.; Tai-Hsiang Chao, Mount Prospect, Ill.; Nancy J. Flint, Wonder Lake, Ill.; Arthur A. Foutsitzis, Des Plaines, Ill.

[73] Assignee: UOP Inc., Des Plaines, Ill.

[21] Appl. No.: 806,984

[22] Filed: Dec. 9, 1985

[51] Int. Cl.$^4$ ............................................. B01J 29/06
[52] U.S. Cl. ...................................... 502/61; 502/71; 502/214
[58] Field of Search ................ 502/61, 71, 214, 64; 585/415

[56] References Cited

U.S. PATENT DOCUMENTS

| | | | |
|---|---|---|---|
| 3,386,801 | 6/1968 | Kuehl | 502/61 |
| 3,507,778 | 4/1970 | Gladrow et al. | 502/64 |
| 3,756,942 | 9/1973 | Cattanach | 208/137 |
| 3,867,279 | 2/1975 | Young | 208/114 |
| 4,152,364 | 5/1979 | Chu | 585/454 |
| 4,157,356 | 6/1979 | Bulford et al. | 585/415 |
| 4,270,017 | 5/1981 | Young | 585/437 |
| 4,350,835 | 9/1982 | Chester et al. | 502/61 |
| 4,567,152 | 1/1986 | Pine | 502/64 |

FOREIGN PATENT DOCUMENTS 2117367 10/1983 United Kingdom ................. 502/61

Primary Examiner—Carl F. Dees
Attorney, Agent, or Firm—Thomas K. McBride; John F. Spears, Jr.

[57] ABSTRACT

Superior tolerance to catalyst coking is obtained with a catalytic composite comprising a gallium component and a crystalline aluminosilicate incorporated with a phorphorus containing alumina. A five-fold reduction in the coke content of the spent catalyst of the instant invention is observed which is directly attributable to the phosphorus containing alumina. A novel method of preparing this catalyst is presented, along with a novel process for the dehydrocyclodimerization of $C_2$-$C_5$ aliphatic hydrocarbons.

15 Claims, No Drawings

PHOSPHORUS CONTAINING ALUMINA CATALYST FOR THE PRODUCTION OF AROMATICS

BACKGROUND OF THE INVENTION

The present invention relates to a novel catalyst composition, and method of manufacturing same, for the dehydrocyclodimerization of $C_2$ to $C_5$ aliphatic hydrocarbons. Additionally a process for producing aromatics via the dehydrocyclodimerization reaction, which utilizes the subject catalyst composition, is disclosed.

Dehydrocyclodimerization is a reaction where reactants comprising paraffins and olefins, containing from 2 to 5 carbon atoms per molecule, are reacted over a catalyst to produce primarily aromatics with $H_2$ and light ends as by-products. This process is quite different from the more conventional reforming or dehydrocyclization process where $C_6$ and higher carbon number reactants, primarily paraffins and naphthenes, are converted to aromatics. These aromatics contain the same or less number of carbon atoms per molecule as the reactants from which they were formed, indicating the absence of reactant dimerization reactions. In contrast, the dehydrocyclodimerization reaction results in an aromatic product that always contains more carbon atoms per molecule than the $C_2$ to $C_5$ reactants, thus indicating that the dimerization reaction is a primary step in the dehydrocyclodimerization process. Typically, the dehydrocyclodimerization reaction is carried out at temperatures in excess of 500° F. using dual functional catalysts containing acidic and dehydrogenation components. These catalysts include acidic amorphous aluminas which contain metal promoters. Recently crystalline aluminosilicates have been successfully employed as catalyst components for the dehydrocyclodimerization reaction. Crystalline aluminosilicates generally referred to as zeolites, may be represented by the empirical formula

$$M_{2/n}\cdot Al_2O_3\cdot xSiO_2\cdot yH_2O$$

in which n is the valence of M which is generally an element of Group I or II, in particular, sodium, potassium, magnesium, calcium, strontium, or barium and x is generally equal to or greater than 2. Zeolites have skeletal structures which are made up of three dimensional networks of $SiO_4$ and $AlO_4$ tetrahedra, corner linked to each other by shared oxygen atoms. The greater the proportion of the $SiO_4$ species to the $AlO_4$ species, the better suited the zeolite is for use as a component in dehydrocyclodimerization catalysts. Such zeolites include mordenite and the ZSM variety. In addition to the zeolite component, certain metal promoters and inorganic oxide matrices have been included in dehydrocyclodimerization catalyst formulations. Examples of inorganic oxides include silica, alumina, and mixtures thereof. Metal promoters such as Group VIII or Group III metals of the Periodic Table, have been used to provide the dehydrogenation functionality. The acidic function can be supplied by the inorganic oxide matrix, the zeolite or both.

Molecular hydrogen is produced in a dehydrocyclodimerization reaction as well as aromatic hydrocarbons. For example, reacting a $C_4$ paraffin will yield 5 moles of hydrogen for every one mole of aromatic produced. Because the equilibrium concentration of aromatics is inversely proportional to the fifth power of the hydrogen concentration, it is desired to carry out the reaction in the absence of added hydrogen. Adherence to this practice, however, promotes rapid catalyst deactivation and, as a result, short catalyst life expectancy. The rapid deactivation is believed to be caused by excessive carbon formation (coking) on the catalyst surface. This coking tendency makes it necessary to frequently perform costly and time-consuming catalyst regeneration. Reducing the coking and thereby increasing catalyst life is the particular object to which this application is directed.

It has now been found that, if a catalyst is formulated with the components, and in the manner set forth hereinafter, an improved process for the dehydrocyclodimerization of $C_2$-$C_5$ aliphatic hydrocarbons will result. The improvements being longer catalyst life expectancy, greater aromatic hyrocarbon yield, and lower catalyst coke levels.

OBJECTS AND EMBODIMENTS

A principal object of our invention is to provide an improved catalyst composition for the dehydrocyclodimerization of aliphatic hydrocarbons. Further, this catalyst composition results in reduced carbon formation, thus improving the overall process of producing aromatics from $C_2$-$C_5$ aliphatic hydrocarbons. Other objects in applying embodiments of the instant invention include providing an efficient and effective catalyst manufacturing procedure. Accordingly, a broad embodiment of the present invention is directed toward a dehydrocyclodimerization catalyst composition comprising phosphorus-containing alumina, a gallium component, and a crystalline aluminosilicate zeolite having a silica to alumina ratio of at least 12.

In another embodiment a method of compositing a catalyst for the dehydrocyclodimerization of $C_2$-$C_5$ aliphatic hydrocarbons is presented which comprises compositing phosphorus, alumina, a gallium component, and a crystalline aluminosilicate having a silica to alumina ratio of at least 12. More specifically, a compositing method comprising (a) mixing a crystalline aluminosilicate with alumina hydrosol, (b) mixing a gelling agent with a phosphorus compound, (c) commingling the mixtures of (a) and (b), (d) dispersing the admixture of step (c) as droplets in a suspending medium under conditions effective to transform said droplets into hydrogel particles and (e) washing, drying and calcining said hydrogel particles to obtain said catalyst composition.

Another embodiment relates to a process for the dehydrocyclodimerization of hydrocarbons which comprises contacting a feed stream containing aliphatic hydrocarbons in the presence of a catalytic composition comprising phosphorus containing alumina, a gallium component, and a crystalline aluminosilicate having a silica to alumina ratio of at least 12.

INFORMATION DISCLOSURE

The prior art recognizes numerous catalyst formulations for the conversion of aliphatic hydrocarbons into aromatic hydrocarbons. Of these catalyst formulations, none embody all of the aspects of the catalytic composition of the present invention nor is it apparent that these prior catalyst formulations have the unique coking tolerance which is characteristic of catalysts of the instant invention. U.S. Pat. No. 3,756,942 teaches the aromatization of $C_5$ and higher number hydrocarbons utilizing the catalyst containing a ZSM-5 type crystalline aluminosilicate. This reference does not mention the utility of incorporating either a gallium component or phosphorus containing alumina in the catalytic composite. It is also important to note that the process claim of the '942 patent is directed to a dehydrocyclization process and specifies that the catalyst is limited to use with feeds comprising from $C_5$ to an upper limit wherein at least 50 volume percent boils no higher than 250° F. This is in contrast to the present invention which is directed at feeds comprising from 2 to 5 carbon atoms per molecule.

The catalyst described in U.S. Pat. No. 4,157,356 does teach the utility of a gallium component for the dehydrocyclodimerization of $C_3$–$C_8$ aliphatic hydrocarbons, but specifically limits the use of gallium to formulations containing solely silica supports. No mention is made of alternative supports or that crystalline aluminosilicates may be utilized.

No references were discovered which identified the use of phosphorus in catalyst formulations specifically used in a dehydrocyclodimerization process. Other references teach the use of phosphorus in catalyst formulations for improving the strength of catalytic composites or to improve the selectivity to a given reaction. U.S. Pat. No. 4,152,364 discloses a method for treating a ZSM-5 type zeolite with a phosphorus compound to deposit at least 0.5 weight percent P onto said zeolite to improve selectivity of a methylating reaction for the production of para-xylene. The '364 patent does not teach use of metals and is specific in that the phosphorus must be added directly to the zeolite. In another reference, U.S. Pat. No. 4,270,017, which is also directed toward a process for the selective production of para-xylene, a catalyst manufacturing method is taught which involves the contacting of a calcined silica polymorph/refractory oxide composite with a phosphorus compound. This method of phosphorus addition to a calcined mixture of silica polymorph and refractory oxide does not yield the catalyst composite of the present invention. The '017 patent also does not teach the use of metals or the use of crystalline aluminosilicate.

Phosphorus is also used as an additive to improve the mechanical integrity of formed catalyst formulations. U.S. Pat. No. 3,867,279 discloses a manufacturing method to prepare a crush resistant catalytic cracking catalyst for converting feeds having initial boiling points of at least 400° F. The '279 patent teaches the addition of a phosphorus compound to a silica sol containing a particulate silicate selected from the group consisting of silica gel, physical mixtures and co-gel of silica and another refractory oxide, and crystalline aluminosilicates. This is distinguished from the catalyst composite of the instant invention in that the '279 patent specifically requires the use of a silica sol in the cracking catalyst formulation.

In brief summation, the prior art which described the use of crystalline aluminosilicates for converting $C_5+$ hydrocarbon feeds, use of gallium metal on a silica support, and addition of phosphorus to strengthen cracking catalyst formulations is not cognizant of the novel catalyst composite, manufacturing, or process use of such composite as described herein.

DETAILED DESCRIPTION OF THE INVENTION

This invention is concerned with the dehydrocyclodimerization of aliphatic hydrocarbons utilizing a novel catalytic composition comprising phosphorus-containing alumina, a gallium component, and crystalline aluminosilicate having a silica to alumina ratio of at least 12. It has been found, surprisingly and unexpectedly, that the instant catalytic composite yields more aromatics, has a longer life expectancy, and cokes less than conventional dehydrocyclodimerization catalysts of the prior art. This lower coking tendency increases the economic attractiveness of the dehydrocyclodimerization process by requiring fewer catalyst regeneration cycles and increasing the on-stream efficiency, thereby increasing the production of aromatics.

In accordance with the present invention, the catalytic composite comprises phosphorus-containing alumina. It is believed and further substantiated in subsequent examples, that this phosphorus-containing alumina is directly responsible for observed reduced catalyst coke levels. The phosphorus may be incorporated with the alumina in any acceptable manner known to those skilled in the art. Examples of such incorporation techniques include pillings, nodulizing, marumerization, spray drying, extrusion, or any combination of these techniques. One preferred method of preparing this phosphorus-containing alumina is in the gelation of a hydrosol precursor in accordance with the well-known oil-drop method. A phosphorus compound is added to an alumina hydrosol to form a phosphorus-containing alumina hydrosol. Representative phosphorus-containing compounds which may be utilized in the present invention include $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or halide. These compounds include primary, $RPH_2$, secondary, $R_2PH$ and tertiary, $R_3P$ phosphines such as butyl phosphine, the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkyl-phosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof, such as the monopropyl ester, alkyl dialkylphosphinites, $(RO)PR_2$ and dialkyl alkylphosphinite, $(RO)_2PR$, esters. Corresponding sulfur derivates may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, $(RO)PCl_2$, dialkylphosphorochloridites, $(RO)_2PCl$, dialkylphosphinochloridites, $R_2PCl$, alkyl alkylphosphonochloridates, (RO)(R)P(O)Cl, dialkylphosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

The amount of phosphorus in the resultant catalytic composite can vary over a wide range. A phosphorous to aluminum ranging from about 1:1 to about 1:100 is preferred. The 1:1 molar ratio corresponds to a phosphorus-containing alumina containing 24.7 wt. % aluminum and 20.5 wt. % phosphorus, while the 1:100 corresponds to 0.6 wt. % phosphorus and 52.0 wt. % aluminum.

The alumina hydrosol is typically prepared by digesting aluminum in aqueous hydrochloric acid and/or aluminum chloride solution at about reflux temperature, usually from about 80° to about 105° C., and reducing the chloride compound concentration of the resulting aluminum chloride solution by the device of maintaining an excess of the aluminum reactant in the reaction mixture as a neutralizing agent. The alumina hydrosol is an aluminum chloride hydrosol variously referred to as an aluminum oxychloride hydrosol, aluminum hydroxychloride hydrosol, and the like, such as is formed when utilizing aluminum metal as a neutralizing agent in conjunction with an aqueous aluminum chloride solution. In any case, the aluminum chloride hydrosol is prepared to contain aluminum in from about a 0.70:1 to about 1.5:1 weight ratio with the chloride compound content thereof.

In accordance with one embodiment of the invention, a phosphorus-containing alumina is prepared by a method which comprises admixing the alumina hydrosol with a phosphorus-containing compound, the phosphorus to aluminum molar ratio in the resulting phosphorus-containing admixture being from 1:1 to 1:100 on an elemental basis and subsequently mixing in a crystalline aluminosilicate and then gelling said admixture to obtain said phosphorus-containing alumina.

In one specific embodiment, the phosphorus compound is mixed with a gelling agent before admixing with the alumina hydrosol. It is preferred that said alumina hydrosol contain a crystalline aluminosilicate. Commingling of the alumina hydrosol, containing said crystalline aluminosilicate, with the phosphorous-gelling agent mixture is effected by any suitable means. Resultant admixture is dispersed as droplets in a suspending medium under conditions effective to transform said droplets into hydrogel particles.

The gelling agent is typically a weak base which, when mixed with the hydrosol, will cause the mixture to set to a gel within a reasonable time. In this type of operation, the hydrosol is typically set by utilizing ammonia as a neutralizing or setting agent. Usually, the ammonia is furnished by an ammonia precursor which is added to the hydrosol. The precursor is suitably hexamethylenetetramine, or urea, or mixtures thereof, although other weakly basic materials which are substantially stable at normal temperatures, but decompose to form ammonia with increasing temperature, may be suitably employed. It has been found that equal volumes of the hydrosol and of the hexamethylenetetramine solution to alumina sol solution are satisfactory, but it is understood that this may vary somewhat. The use of a smaller amount of hexamethylenetetramine solution tends to result in soft spheres while, on the other hand, the use of larger volumes of base solution results in spheres which tend to crack easily. Only a fraction of the ammonia precursor is hydrolyzed or decomposed in the relatively short period during which initial gelation occurs.

An aging process is preferably subsequently employed. During the aging process, the residual ammonia precursor retained in the spheroidal particles continues to hydrolyze and effect further polymerization of the hydrogel whereby desirable pore characteristics are established. Aging of the hydrogel is suitably accomplished over a period of from about 1 to about 24 hours, preferably in the oil suspending medium, at a temperature of from about 60° to about 150° C. or more, and at a pressure to maintain the water content of the hydrogel spheres in a substantially liquid phase. The aging of the hydrogel can also be carried out in aqueous $NH_3$ solution at about 95° C. for a period up to about 6 hours. Following the aging step the hydrogel spheres may be washed with water containing ammonia.

The phosphorus-containing alumina of the present invention may also contain minor proportions of other wellknown inorganic oxides such as silica, titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria, and the like materials which can be added to the hydrosol prior to dropping.

Another embodiment of the present invention is that the catalytic composite contain a gallium component. This component may be present in any form including elemental metal, oxide, hydroxide, halide, oxyhalide, aluminate, or in chemical combination with one or more of the other ingredients of the catalytic composite. Although it is not intended to restrict the present invention by this explanation, it is believed that the best results are obtained when the gallium component is present in the composite in the zero valency state. This gallium component can be used in any amount which is catalytically effective with good results obtained, on an elemental basis, with about 0.1 to about 5% gallium by weight of the total catalytic composite. Best results are ordinarily achieved with about 0.5 to 1 wt. % gallium, calculated on an elemental basis. Although not a necessary condition of the present invention, it is believed that a substantial portion of the gallium present in the catalyst composite is located in and/or on the crystalline aluminosilicate component.

This gallium component may be incorporated in the catalytic composite in any suitable manner known to the art to result in a relatively uniform dispersion of the gallium, such as, by ion exchange, cogelation, or impregnation either after, before, or during the compositing of the catalyst formulation. It is to be noted that it is intended to include within the scope of the present invention all conventional methods for incorporating and simultaneously uniformly distributing a metallic component in a catalytic composite and the particular method of incorporation used is not deemed to be an essential feature of the present invention. A preferred method of incorporating the gallium involves ion exchange of the crystalline aluminosilicate with a soluble, decomposite compound of gallium, such as, gallium tribromide, gallium perchlorate, gallium trichloride, gallium hydroxide, gallium nitrates, gallium oxalate, and the like compounds.

As mentioned hereinabove, crystalline aluminosilicate zeolites have been successfully employed as components in dehydrocyclodimerization catalysts. In particular, a family of crystalline aluminosilicates are preferred, specifically those with silica to alumina ratios of at least 12. A particularly preferred family is the one identified as the ZSM variety. Included among this ZSM variety are ZSM-5, ZSM-8, ZSM-11, ZSM-12, ZSM-35, and other similarly behaving zeolites. It is most preferred that ZSM-5 be utilized as the crystalline aluminosilicate component of the present invention. These ZSM type zeolites are generally prepared by crystallizing a mixture containing a source of alumina, a source of silica, a source of alkali metal, water, and a tetraalkylammonium compound or its precursors. Of course, other crystalline aluminosilicates which meet the silica to alumina ratio criteria may be used, such as, faujasites, L-type, mordenites, omega-type, and the like. The relative proportions of the crystalline aluminosilicate zeolite and the other components of the catalytic composite vary widely with the zeolite content ranging from about 40 percent to about 80 percent by weight and more preferably in the range from about 50 to 70 percent by weight of composite.

The catalytic composite of the instant invention may be shaped into any useful form, such as, spheres, pills, cakes, extrudates, powders, granules, tablets, etc., and utilized in any desired size. Formation usually occurs during the compositing of the catalytic components, following any known method in the art. For the purposes of the present invention, a particular useful shape of the subject catalytic composite is the sphere, manufactured by the well-known oil drop method which comprises: forming an alumina hydrosol by any of the techniques taught in the art and preferably by reacting aluminum metal with hydrochloric acid, combining the resultant hydrosol with the crystalline aluminosilicate zeolite. This alumina zeolite hydrosol is commingled with a suitable gelling agent which has been contacted with a phosphorus-containing compound as previously set forth hereinabove. The resultant admixture is dispersed as droplets into an oil bath maintained at elevated temperatures. The droplets of the mixture remain in the oil bath until they set and form hydrogel spheres. The spheres are continuously withdrawn from the oil bath and typically subjected to specific aging treatments in oil and an ammoniacal solution to further improve their physical characteristics. The resulting aged and gelled particles are then washed and dried at a relatively low temperature of about 150° to about 205° C. and subjected to a calcination procedure at a temperature of about 450° C. to about 700° C. for a period of about 1 to about 20 hours. This treatment effects conversion of the hydrogel spheres to the desired phosphorus-containing alumina composite. See the teachings of U.S. Pat. No. 2,620,314 for additional details.

The dehydrocyclodimerization conditions which will be employed for use with the catalyst composition of the present invention will, of course, vary depending on such factors as feedstock composition and desired conversion. A desired range of conditions for the dehydrocyclodimerization of $C_2$–$C_5$ aliphatic hydrocarbons to aromatics include a temperature from about 350° C. to about 650° C., a pressure from about 1 to about 20 atmospheres, and a liquid hourly space velocity from about 0.2 to about 5 hr.$^{-1}$. The preferred process conditions are a temperature in the range from about 400° to 550° C., a pressure in or about the range from 2 to 10 atmospheres and a liquid hourly space velocity of between 0.5 to 2.0 hr.$^{-1}$. It is understood that, as the average carbon number of the feed increases, a temperature in the lower end of temperature range is required for optimum performance and conversely, as the average carbon number of the feed decreases, the higher the required temperature.

The feed stream to the dehydrocyclodimerization process is defined herein as all streams introduced into the dehydrocyclodimerization reaction zone. Included in the feed stream is the $C_2$–$C_5$ aliphatic hydrocarbon. By $C_2$–$C_5$ aliphatic hydrocarbons is meant one or more open, straight or branched chain isomers having from about two to five carbon atoms per molecule. Furthermore, the hydrocarbons in the feedstock may be saturated or unsaturated. Preferably, the hydrocarbons $C_3$ and/or $C_4$ are selected from isobutane, normal butane, isobutene, normal butene, propane and propylene. Diluents may also be included in the feed stream. Examples of such diluents include hydrogen, nitrogen, helium, argon, neon, CO, $CO_2$, $H_2O$ or its precursors. Water precursors are defined as those compounds which liberate $H_2O$ when heated to dehydrocyclodimerization reaction temperatures.

According to the present invention, the feed stream is contacted with the instant catalytic composite in a dehydrocyclodimerization reaction zone maintained at dehydrocyclodimerization conditions. This contacting may be accomplished by using the catalytic composite in a fixed bed system, a moving bed system, a fluidized bed system, or in a batch type operation; however, in view of the danger of attrition losses of the valuable catalyst and of the wellknown operational advantages, it is preferred to use either a fixed bed system or a dense-phase moving bed system such as shown in U.S. Pat. No. 3,725,249. It is contemplated that the contacting step can be performed in the presence of a physical mixture of particles of the present invention catalyst composite and particles of another dehydrocyclodimerization or similarly behaving catalyst of the prior art.

In a fixed bed system or a dense-phase moving bed the feed stream is preheated by any suitable heating means to the desired reaction temperature and then passed into a dehydrocyclodimerization zone containing a bed of the instant catalytic composite. It is, of course, understood that the dehydrocyclodimerization zone may be one or more separate reactors with suitable means therebetween to assure that the desired conversion temperature is maintained at the entrance to each reactor. It is also important to note that the reactants may be contacted with the catalyst bed in either upward, downward, or radial flow fashion with the latter being preferred. In addition, the reactants may be in the liquid phase, admixed liquid-vapor phase, or a vapor phase when they contact the catalyst, with the best results obtained in the vapor phase. The dehydrocyclodimerization system then preferably comprises a dehydrocyclodimerization zone containing one or more fixed or dense-phase moving beds of the instant catalytic composite. In a multiple bed system, it is, of course, within the scope of the present invention to use the present catalyst composite in less than all of the beds with another dehydrocyclodimerization or similarly behaving catalyst being used in the remainder of the beds. This dehydrocyclodimerization zone may be one or more separate reactors with suitable heating means therebetween to compensate for any heat loss encountered in each catalyst bed. Specific to the dense-phase moving bed system, it is common practice to remove catalyst from the bottom of the reaction zone, regenerate it by conventional means known to the art, and then return it to the top of the reaction zone.

The following example will serve to illustrate certain specific embodiments of the herein disclosed invention. This example should not, however, be construed as limiting the scope of the invention as set forth in the claims as there are many variations which may be made thereon without departing from the spirit of the invention, as those of skill in the art will recognize.

EXAMPLE

To demonstrate the superior tolerance to coking which is characteristic of catalysts made in accordance with the instant invention, Catalyst A was formulated as follows. A first solution was prepared by adding phosphoric acid to an aqueous solution of hexamethylenetetramine (HMT) in an amount to yield a phosphorus content of the finished catalyst equal to about 11 wt. %. A second solution was prepared by adding a ZSM-5 type zeolite to enough alumina sol, prepared by digesting metallic aluminum in hydrochloric acid, to yield a zeolite content in the finished catalyst equal to about 67 wt. %. These two solutions were commingled to achieve a homogenous admixture of HMT, phosphorus, alumina sol, and zeolite. This admixture was dispersed as droplets into an oil bath maintained at about 200° F. The droplets remained in the oil bath until they set and formed hydrogel spheres. These spheres were removed from the oil bath, water washed, air dried, and calcined at a temperature of about 900° F. A solution of gallium nitrate was utilized to impregnate the spheres to achieve a gallium content on the finished catalyst equal to about 1 wt. %. After impregnation the spheres were calcined a second time, in the presence of steam, at a temperature of about 1200° F.

A second catalyst was formulated as a conventional dehydrocyclodimerization catalyst to further illustrate the superior tolerance to coking of catalysts of the subject invention. This catalyst was designated as Catalyst B and was not made in accordance with the instant invention. Catalyst B was prepared in substantially the same manner as Catalyst A, but without the addition of a phosphorus compound.

Catalysts A and B were tested for dehydrocyclodimerization performance in identically the same manner using a flow reactor processing a feed comprising 85% n-$C_4$ and 15% i-$C_4$. The operating conditions used in the performance test comprised a reactor pressure of 75 psig, a liquid hourly space velocity of 2 $hr^{-1}$, and a reaction zone inlet temperature of about 1000° F. The conversion of the feed, the selectivity to aromatic compounds and the catalyst coke content after 100 hours of operation were measured. The table which follows summarizes the results for each catalyst.

|  | P. wt. % | Avg. Selectivity wt. % | Avg. Conversion wt. % | 1. Coke wt. % |
|---|---|---|---|---|
| Catalyst A | 11 | 57 | 45 | 5.8 |
| Catalyst B | — | 54 | 45 | 30.5 |

1. Measured analytically as elemental carbon.

Although the convention and selectivity results for each catalyst are nearly equal, there is more than a five-fold reduction of the catalyst coke content for Catalyst A. This clearly illustrates that a catalyst composite made in accordance with the invention set forth herein demonstrates a much higher tolerance to catalyst coking than does a catalyst made via a conventional formulation. This reduction in coke make allows for longer catalyst life leading to greater overall aromatic yield.

We claim:

1. A catalytic composition for the dehydrocyclodimerization of $C_2$-$C_5$ aliphatic hydrocarbons comprising phosphorus containing alumina, a gallium component, and crystalline aluminosilicate zeolite having a silica to alumina ratio of at least 12.

2. The catalytic composition of claim 1 further characterized in that the crystalline aluminosilicate zeolite is of the ZSM variety.

3. The catalytic composition of claim 1 further characterized in that the crystalline aluminosilicate zeolite is ZSM-5.

4. The catalytic composition of claim 1 further characterized in that the gallium is present in an amount ranging from about 0.1-5.0 percent by weight of the total catalytic composite.

5. True catalytic composition of claim 1 further characterized in that the phosphorus containing alumina is present in an amount between 40 and 60 percent by weight of the total catalytic composite.

6. The catalytic composition of claim 1 further characterized in that the phosphorus to aluminum ratio of the phosphorus containing alumina is from 1:1 to 1:100.

7. A method of manufacturing a catalytic composition for the dehydrocyclodimerization of $C_2$-$C_5$ aliphatic hydrocarbons which comprises compositing phosphorus, alumina, a gallium component, and crystalline aluminosilicate zeolite having a silica to alumina ratio of at least 12.

8. The method of claim 7 wherein the gallium component is added to the crystalline aluminosilicate zeolite in an amount to acheive an elemental gallium content of from about 0.5 to about 12 percent by weight of said crystalline aluminosilicate zeolite.

9. The method of claim 7 whrein the gallium component is added to an admixture of said phosphorus containing alumina and said crystalline aluminosilicate zeolite by means to achieve an elemental gallium content of between 0.5 and 5.0 percent by weight of said catalytic composition.

10. A method of manufacturing a catalytic composition for the dehydrocyclodimerization of $C_2$-$C_5$ aliphatic hydrocarbons comprising:
   (a) depositing a gallium component onto crystalline aluminosilicate zeolite powder to achieve an elemental gallium content between 0.5 and 12 wt. % of said crystalline aluminosilicate zeolite powder;
   (b) mixing said gallium containing aluminosilicate zeolite powder with aluminum hydrosol;
   (c) mixing a gelling agent with a phosphorus compound;
   (d) commingling the mixtures of steps (b) and (c);
   (e) dispersing the admixture of step (d) as droplets in a suspending medium under conditions effective to transform said droplets into hydrogel particles; and
   (f) aging, washing, drying, and calcining said hydrogel particles to obtain said catalytic composition.

11. The method of claim 10 wherein the gelling agent is hexamethylenetetramine.

12. The method of claim 10 wherein the alumina hydrosol is prepared by digesting metallic aluminum in hydrochloric acid.

13. A method of manufacturing a catalytic composition for the dehydrocyclodimerization of $C_2$-$C_5$ aliphatic hydrocarbons comprising:

(a) mixing crystalline aluminosilicate zeolite powder with aluminum hydrosol;
(b) mixing a gelling agent with a phosphorus compound;
(c) comingling the mixtures of steps (a) and (b);
(d) dispersing the admixture of step (c) as droplets in a suspending medium under conditions effective to transform said droplets into hydrogel particles;
(e) aging, washing, drying, and calcining said hydrogel particles to obtain calcined particles; and
(f) thereafter depositing a gallium component onto said calcined particles to achieve an elemental gallium content of between 0.5 and 5.0 percent by weight of said catalytic composition.

14. The method of claim 13 wherein the gelling agent is hexamethylenetetramine.

15. The method of claim 13 wherein the alumina hydrosol is prepared by digesting metallic aluminum in hydrochloric acid.

* * * * *